US007585520B2

(12) United States Patent
Hirsh et al.

(10) Patent No.: US 7,585,520 B2
(45) Date of Patent: *Sep. 8, 2009

(54) COMPOSITIONS CONTAINING BOTH SEDATIVE AND NON-SEDATIVE ANTIHISTAMINES AND SLEEP AIDS

(75) Inventors: Mark Hirsh, Wellesley, MA (US); Jane Hirsh, Wellesley, MA (US); Whe-Yong Lo, Canton, MA (US)

(73) Assignee: Collegium Pharmaceutical, Inc., Cumberland, RI (US)

( * ) Notice: Subject to any disclaimer, the term of this patent is extended or adjusted under 35 U.S.C. 154(b) by 658 days.

This patent is subject to a terminal disclaimer.

(21) Appl. No.: 10/943,311

(22) Filed: Sep. 17, 2004

(65) Prior Publication Data

US 2005/0069580 A1    Mar. 31, 2005

Related U.S. Application Data

(63) Continuation-in-part of application No. 10/012,202, filed on Dec. 5, 2001, now Pat. No. 6,827,946.

(51) Int. Cl.
*A61K 9/24* (2006.01)
*A61K 9/20* (2006.01)
*A61K 9/22* (2006.01)
*A61K 9/28* (2006.01)
*A61K 9/14* (2006.01)

(52) U.S. Cl. .................. 424/472; 424/464; 424/465; 424/468; 424/474; 424/489; 424/490

(58) Field of Classification Search ................. 424/472, 424/464
See application file for complete search history.

(56) References Cited

U.S. PATENT DOCUMENTS

| | | |
|---|---|---|
| 2,297,599 A | 9/1942 | Wilen |
| 3,873,727 A | 3/1975 | Fusari et al. |
| 3,898,323 A | 8/1975 | Fennell et al. |
| 4,004,036 A | 1/1977 | Schmitt |
| 4,139,589 A | 2/1979 | Beringer et al. |
| 4,229,447 A | 10/1980 | Porter |
| 4,322,433 A | 3/1982 | Leslie et al. |
| 4,571,395 A | 2/1986 | Peck |
| 4,619,934 A | 10/1986 | Sunshine |
| 4,661,492 A | 4/1987 | Lewis et al. |
| 4,783,465 A | 11/1988 | Sunshine |
| 4,814,181 A | 3/1989 | Jordan et al. |
| 5,053,032 A | 10/1991 | Barclay et al. |
| 5,064,656 A | 11/1991 | Gergely et al. |
| 5,082,667 A | 1/1992 | Van Scoik |
| 5,156,850 A | 10/1992 | Wong et al. |
| 5,248,310 A | 9/1993 | Barclay et al. |
| 5,294,433 A | 3/1994 | Singer et al. |
| 5,314,697 A | 5/1994 | Kwan |
| 5,362,496 A | 11/1994 | Baker et al. |
| 5,368,588 A | 11/1994 | Bettinger et al. |
| 5,369,588 A | 11/1994 | Hayami et al. |
| 5,385,941 A | 1/1995 | Fawzi |
| 5,407,339 A | 4/1995 | Fehlhafer |
| 5,407,686 A | 4/1995 | Patel et al. |
| 5,451,409 A * | 9/1995 | Rencher et al. ............ 424/468 |
| 5,512,293 A | 4/1996 | Landrau et al. |
| 5,512,299 A | 4/1996 | Place et al. |
| 5,558,879 A | 9/1996 | Chen et al. |
| 5,573,776 A | 11/1996 | Harrison et al. |
| 5,595,997 A | 1/1997 | Aberg |
| 5,609,884 A | 3/1997 | Desai |
| 5,648,358 A * | 7/1997 | Mitra .................... 514/263.32 |
| 5,656,284 A | 8/1997 | Balkin |
| 5,702,723 A | 12/1997 | Griffin |
| 5,739,136 A | 4/1998 | Ellinwood, Jr. et al. |
| 5,756,125 A | 5/1998 | Desai |
| 5,776,493 A | 7/1998 | Barclay et al. |
| 5,807,579 A | 9/1998 | Vilkov |
| 5,827,180 A | 10/1998 | Goodman |
| 5,827,852 A * | 10/1998 | Russell et al. ............... 514/162 |

(Continued)

FOREIGN PATENT DOCUMENTS

EP    0 584 594    3/1994

(Continued)

OTHER PUBLICATIONS

Hackhs, "Chemical Dictionary", 2$^{nd}$ Edition, pp. 185-186 (Jun. 30, 1938).

(Continued)

*Primary Examiner*—Humera N Sheikh
(74) *Attorney, Agent, or Firm*—Pabst Patent Group LLP

(57) ABSTRACT

Compositions containing both a sedative compound and a non-sedative antihistamine are provided. More particularly, compositions for administration at bedtime containing a sedating antihistamine or other sedating compound in immediate release form and a non-sedating antihistamine in delayed-release form are described. Alternatively, a composition, for administrating upon awakening, containing a non-sedating antihistamine in immediate release form, and a sedating antihistamine or other sedative in delayed-release form is described. Methods of inhibiting the release of histamines by administration of the compositions to a mammalian subject are also provided. The dosage forms may comprise other medications, such as leukotriene receptor antagonists, to enhance the suppression of histamine symptoms.

15 Claims, No Drawings

U.S. PATENT DOCUMENTS

| | | |
|---|---|---|
| 5,900,421 A | 5/1999 | Handley |
| 6,004,582 A | 12/1999 | Faour et al. |
| 6,039,974 A | 3/2000 | Maclaren |
| 6,051,585 A | 4/2000 | Weinstein |
| 6,054,463 A | 4/2000 | Handley |
| 6,086,914 A | 7/2000 | Weinstein |
| 6,110,500 A | 8/2000 | Kim |
| 6,114,346 A | 9/2000 | Harris |
| 6,124,320 A | 9/2000 | Woosley |
| 6,130,233 A | 10/2000 | Woosley |
| 6,166,037 A | 12/2000 | Budhu |
| 6,183,778 B1 | 2/2001 | Conte et al. |
| 6,294,199 B1 | 9/2001 | Conley et al. |
| 6,372,254 B1 | 4/2002 | Ting et al. |
| 6,372,255 B1 | 4/2002 | Saslawski et al. |
| 6,379,651 B1 | 4/2002 | Athanikar |
| 6,572,891 B1 | 6/2003 | Ugarkovic |
| 6,602,518 B2 | 8/2003 | Seielstad et al. |
| 6,827,946 B2 * | 12/2004 | Hirsh ..................... 424/472 |
| 6,863,901 B2 | 3/2005 | Hirsh et al. |
| 2001/0002999 A1 | 6/2001 | Neuser et al. |
| 2003/0143257 A1 | 7/2003 | Fleshner-Barak et al. |

FOREIGN PATENT DOCUMENTS

| | | |
|---|---|---|
| EP | 1 044 680 | 10/2000 |
| EP | 1 112 737 | 7/2001 |
| FR | 2 772 615 | 6/1999 |
| GB | 800 973 | 9/1958 |
| WO | WO 98/46235 | 10/1998 |
| WO | WO 99/15173 | 4/1999 |
| WO | WO 00/35296 | 6/2000 |
| WO | WO 01/37814 | 5/2001 |
| WO | WO 01/45688 | 6/2001 |

OTHER PUBLICATIONS

Remington's Pharmaceutical Sciences, Eighteenth Edition, p. 844 (1990).

Onur Feyyaz, et al., "Simultaneous determination of pseudoephedrine sulfate dexbrompheniramine maleate and loratadine in pharmaceutical preparations using derivative spectrophotometry and ratio spectra derivative spectrophotometry", *Talanta* 51(2):269-279 (2000).

* cited by examiner

COMPOSITIONS CONTAINING BOTH SEDATIVE AND NON-SEDATIVE ANTIHISTAMINES AND SLEEP AIDS

CROSS-REFERENCE TO RELATED APPLICATIONS

This application is a continuation-in-part of U.S. Ser. No. 10/012,202, filed Dec. 5, 2001 now U.S. Pat. No. 6,827,946, entitled "Compositions Containing Both Sedative and Non-Sedative Antihistamines" by Mark Hirsh, Jane Hirsh, and Whe-Yong Lo.

BACKGROUND OF THE INVENTION

Hypersensitivity is an immune response after exposure to an antigen. Hypersensitivity usually causes tissue damage. Typical hypersensitivity reactions are allergic rhinitis, allergic conjunctivitis, urticaria, pruritus, sinusitis, angioedema, and anaphylaxis. Antihistamines, normally classified as $H_1$ receptor antagonists, are used for the prophylaxis and relief of symptoms of hypersensitivity reactions.

The term "antihistamine" is generally applied to Histamine $H_1$ receptor antagonists. There are two types of antihistamines: first generation and second generation. The older antihistamines (first generation antihistamines) are associated with troublesome sedative and anti-muscarinic effects and are often called sedating antihistamines. These older antihistamines are distinguished from the newer (second generation) antihistamines which are essentially devoid of the sedative effect and are usually termed "non-sedating antihistamines".

Both groups of antihistamines are commonly used. Many sedating antihistamines are widely used and are available over the counter. Typical first generation antihistamines include, without limitation, brompheniramine, chlorpheniramine, dexbrompheniramine, dexchlorpheniramine, carbinoxamine, clemastine, diphenhydramine, pyrilamine, tripelennamine, tripolidine, methdilazine, bromodiphenhydramine, promethazine, azatadine, cyproheptadine, diphenylpyraline, doxylamine, trimeprazine, phenindamine, hydroxyzine, ketotifen, tazifylline, meclazine, setastine, oxatomide, levocarbastine, lodoxamide, pheniramine, propiomazine, emedastine, flunarizine, meclozine, mefenidramine, methylsulfate and mepyramine.

Typical second generation antihistamines include, without limitation, fexofenadine, loratadine, descarboethoxyloratadine, norastemizole, desmethylastemizole, cetirizine, acrivastine, ketotifen, temelastine, ebastine, epinastine, mizolastine, and setastine, astemizole, levocetirizine, rupatadine, mizolastin, noberastine and mequitazine. Cetirizine, in spite of being a second generation antihistamine, has a low to moderate sedative effect.

The sedative effect of the sedating antihistamines can range from slight drowsiness to deep sleep. Daytime sedation can be a problem especially for those who drive or who operate machinery. In view of these problems with sedative antihistamines, non-sedative antihistamines have been developed. This group of compounds has little or no sedative effect and has replaced the first generation antihistamines, especially for daytime use. The major disadvantage of the non-sedating antihistamines is the occurrence of drug interactions and hazardous ventricular arrhythmias which has led to the withdrawal of two non-sedating antihistamines from the market.

Although the non-sedating antihistamines have been widely used for daytime control of allergies, the sedative effect of sedating antihistamines may be preferred by patients who suffer from insomnia or by patients who need a good night sleep. It may be especially advantageous to administer a sedating antihistamine in combination with a decongestant, such as phenylephrine, since decongestants such as phenylephrine often stimulate nervousness and anxiety in a patient. Thus, distinct advantages can be found in the use of "first generation antihistamines" and "second generation antihistamines."

Some antihistamines have a long duration of action, either directly or via long-lived active metabolites. These antihistamines, upon repeated administration (for example, daily), build up in the blood stream to provide a relatively constant steady state level of antihistamine effect at all times during the day and night. The table below shows the elimination half-life of some common non-sedating H1 antihistamines:

TABLE 1

Elimination Half-Life of Non-Sedating H1 Antihistamines

| Drug (Active Metabolite) | Elimination half-life (hours) |
|---|---|
| Acrivastine | 1.4-2.1 |
| Astemizole | 20-30 |
| Desmethylastemizole | 290 |
| Ceterizine | 7-10 |
| Ebastine | 13-16 |
| Fexofenadine | 11-15 |
| Loratidine | 7.8-11 |
| Descarboethoxyloratidine | 17.3-24 |
| Mizolazine | 8-13 |

When the non-sedating antihistamine, or its metabolite, has a long half life (for example, the Loratadine metabolite Descarboethoxyloratadine), plasma levels reach a steady state after repeated use and as a result there are minimal changes in $C_{min}$ and $C_{max}$. In those cases where one daily dose of a non-sedating antihistamine provides 24 hour relief, a dose of a sedating antihistamine can be followed within a few hours, for example within the first eight hours after ingestion, preferably within the first six hours, and more preferably by the beginning of the release of the non-sedating antihistamine. At this point, the release of the sedating and non-sedating antihistamines are overlapping and as a result their effects are additive. The sedating antihistamine provides for a greater antihistamine efficacy and advantageous side effect profile (e.g. sedation). The non-sedating antihistamine provides for 24 hour antihistamine coverage due to its long half life and its lack of sedation as a side effect. The short delay of the non-sedating antihistamine remains important to ensure that the peak plasma level ($C_{max}$) that occurs at dosing does not occur at the time the patient is attempting to fall asleep. The timing of the delayed release of the non-sedating antihistamine will depend on the duration of the antihistamine action of the sedating antihistamine.

When the long half-life antihistamine is a non-sedating antihistamine, a sedative can be used alone or in combination with a sedating antihistamine to induce sleep. Antidepressants, in low dosages, can have a sedative effect. Suitable antidepressants, which can be used alone or in combination with a sedating-antihistamine, include tricyclic/polycyclic antidepressants such as doxepin or selective serotonin reuptake inhibitors such as trazodone. Doxepin is a histamine H1-H2-receptor antagonist, and in doses ranging from 5-25 mg can cause side effects ranging from drowsiness to sedation. Trazodone, when used as an antidepressant, has a typical dosage range of 150-400 mg. However, Trazodone, when administered in sub-therapeutic doses of 12.5 mg to 25 mg, can cause side effects ranging from drowsiness to sedation. Additionally, anxiolytic and hypnotic drugs such as hydroxyzine or diazepam can produce effects ranging from pleasant drowsiness to direct sedation.

The combination of an antihistamine with a decongestant is well known. U.S. Pat. No. 5,314,697 to Kwan et al. discloses compositions that contain the non-sedating antihistamine loratadine and the decongestant pseudoephedrine. Such compositions contain loratadine in a film coating for immediate release and pseudoephedrine in a core surrounded by the film coating so that the pseudoephedrine is released over an extended period. However, Kwan does not describe a composition that contains both a sedating antihistamine and a non-sedating antihistamine.

One of the most common side effects of sedating antihistamines, depending on the specific drug and its dose, is central nervous system (CNS) depression, with effects varying from slight drowsiness to deep sleep. The sedating antihistamines can also cause dizziness and a lack of coordination. These sedative properties of the first generation antihistamines interfere with the normal functioning of patients suffering from allergies. These patients have to be alert and remain ambulatory throughout the day. Therefore the use of first generation antihistamines, in spite of their unique and useful antihistaminic properties, has been limited.

U.S. Pat. No. 6,114,346 to Harris et al. discloses compositions containing the non-sedating antihistamine desloratadine and which may further contain a decongestant including phenylephrine, pseudoephedrine, and phenylpropanolamine. Such compositions are administered to patients afflicted with upper airway passage allergic inflammation associated with allergic rhinitis to treat or prevent sleep disorder. However, Harris does not describe compositions containing both a sedating antihistamine and a non-sedating antihistamine or to use such a composition to inhibit the release of histamine throughout the day and night.

U.S. Pat. No. 6,051,585 to Weinstein et al. discloses compositions administered once a day in a single oral dosage, containing a decongestant and an antihistamine, for example a non-sedating antihistamine such as loratadine or fexofenadine. Weinstein, however, does not describe a composition that includes both a sedating antihistamine and a non-sedating antihistamine.

U.S. Pat. No. 6,086,914 to Weinstein et al. discloses antihistamine compositions that contain a non-sedating antihistamine as well as a specific anticholinergic agent. Preferred examples of specific anticholinergic agents include belladona extracts such as atropine and scopolamine. None of the anticholinergic agents disclosed in this reference, however, is itself a sedating antihistamine and therefore the compositions disclosed are "essentially non-sedating."

U.S. Pat. No. 5,648,358 to Mitra discloses antihistamine compositions that may contain a mixture of one or more sedating antihistamines including clemastine fumarate as well as an additional sedating antihistamine and a non-sedating antihistamine such as loratidine. The compositions also contain caffeine. Mitra, however, does not disclose the delayed release of either the sedating antihistamine or the non-sedating antihistamine.

U.S. Pat. No. 5,827,852 to Russell broadly discloses coated pharmaceutical compositions that may include mixtures of active ingredients including sedating and non-sedating antihistamines. Once again there is no disclosure of the delayed release of either the sedating antihistamine or the non-sedating antihistamine.

U.S. Pat. No. 6,262,077 to Shih discloses compositions for treatment of asthma, allergic rhinitis and related disorders comprising in combination a leukotriene receptor antagonist with a neurokinin antagonist. No sedating effects are disclosed or discussed.

Nelson, *J. Allergy & Clin. Immunology* 112(4), S96-S100 October 203), "Prospects for antihistamines in the treatment of asthma", describes improvement in asthma control with montelukast, a leukotriene receptor antagonist, by co-administration with loratidine, a non-sedating antihistamine. As described in the abstract, the combination is thought to minimize the sedating effects of high levels of even non-sedating antihistamines, by reducing the amount required. Nelson, however, does not describe compositions containing a sedating and non-sedating antihistamine.

It is therefore an object of the invention to provide a once daily oral dosage form which provides both sedating and non-sedating antihistamines for night and daytime histamine control.

It is an object of the invention to provide a once-daily oral dosage form for night and daytime histamine control which comprises a long-lasting non-sedating antihistamine and a sedating non-histamine substance.

It is an object of the invention to provide a once daily oral dosage form which provides both one or more sedating compounds, histamine and/or non-histamine, and at least one non-sedating antihistamine for night and daytime histamine control, the dosage form further comprising a leukotriene receptor antagonist for enhanced control of symptoms.

It is a further object of the invention to enable the use of a once-a-day treatment for the symptoms of histamine release which may act either by the inhibition of the release of histamine, or by the prevention of the action of released histamine, or by another method that relieves the symptoms of histamine release.

It is a further object of the invention to provide a composition that is administered to a patient once-a-day so as to improve the ease of administration and thus increase the rate of patient compliance.

It is a further object of the invention to provide a composition that is designed to be administered once a day, either in the morning or in the evening.

BRIEF SUMMARY OF THE INVENTION

Compositions containing both a sedative compound and a non-sedative antihistamine are provided. More particularly, compositions for administration at bedtime contain a sedating antihistamine or other sedating compound in immediate release form and a non-sedating antihistamine in delayed-release form. Alternatively, a composition for administration upon awakening, contains a non-sedating antihistamine in immediate release form, and a sedating antihistamine or other sedative in delayed-release form. Methods of inhibiting the release of histamines by administration of the compositions are also provided. The dosage forms may comprise other medications, such as leukotriene receptor antagonists, to enhance the suppression of histamine symptoms.

DETAILED DESCRIPTION OF THE INVENTION

Compositions of Sedating and Non-Sedating Antihistamines

A preferred approach is to utilize the properties of sedative antihistamines by administering such sedatives to induce or maintain sleep during the night, and to use non-sedating antihistamines to provide antihistamine effects during the day. Broadly speaking, when a composition is administered right before bedtime (the "PM" dosage form, but for use at bedtime whenever that might occur in the day), the sedating properties of a sedating antihistamine, begin within about the first hour after ingestion, and provide sedation either by prompt release or by controlled release, or a combination thereof, for a first duration of about 2 to 4 hours, preferably up to about 6 hours or 8 hours. At a determined time after the initial administration, when the patient needs to be awake, non-sedating antihistamines are released from the composition, or released at a greater rate, to provide the beneficial effect of an antihistamine, thereby permitting the patient to avoid sedation during the time period in which the patient wishes to remain alert to carry out normal functions as necessary during the day.

In one aspect of a PM dosage form, when the sedative is a sedative antihistamine, the release of the non-sedating antihistamine is delayed, or is initially limited in quantity, to properly control the total antihistamine level. For example, the release of sedative antihistamine will begin immediately, or within one hour, and the dose will be sufficient to sustain a sedating effect for a duration of at least one hour, preferably two hours or more, more preferably for about 2 hours to 6 hours, and optionally for a longer period of about 6 hours to 10 hours. If required, the sedating antihistamine will be at least partially present as a delayed release form or as a sustained release form, if required to achieve the required period of activity for effective sedation.

The non-sedating antihistamine's release can then begin almost immediately, or within an hour. More preferably, its release will begin at a time in the range of 2 to 6 hours after administration, as the effect of the sedating antihistamine wears off. The non-sedating antihistamine will then provide an effective level of antihistamine response for a duration which preferably extends until it is time for the next dose, i.e., about 24 hours after the administration. When the release of the non-sedating antihistamine overlaps that of the sedating antihistamine, the rate of release, or the amount released, may be controlled to a certain extent to prevent an excessive rise in antihistamine levels, and later increase to a higher rate or amount to provide an effective dose.

Examples of the sedating antihistamines that may be employed include brompheniramine, chlorpheniramine, dexbrompheniramine, dexchlorpheniramine, carbinoxamine, clemastine, diphenhydramine, pyrilamine, tripelennamine, tripolidine, methdilazine, bromodiphenhydramine, promethazine, azatadine, cyproheptadine, diphenylpyraline, doxylamine, trimeprazine, phenindamine, hydroxyzine, ketotifen, tazifylline, meclazine, setastine, oxatomide, levocarbastine, lodoxamide, pheniramine, propiomazine, emedastine, flunarizine, meclozine, mefenidramine, methylsulfate and mepyramine.

Examples of the non-sedating antihistamines that may be employed include fexofenadine, loratadine, descarboethoxyloratadine, norastemizole, desmethylastemizole, cetirizine, acrivastine, ketotifen, temelastine, ebastine, epinastine, mizolastine, norrberastine, setastine, astemizole, levocetirizine, rupatadine, mizolastin and mequitazine.

Examples of the decongestants that may be employed include pseudoephedrine, phenylephrine, and pharmaceutically acceptable acid addition salts thereof including the hydrochloride, hydrobromide, bitartrate, and tannate salts.

Substitution of Sedative and Antihistamine for Sedating Antihistamine

When the sedative is not an antihistamine, the timing of its release and duration is essentially the same as that of a sedative antihistamine. The timing of the release of the non-sedating antihistamine then becomes relatively flexible, and the essential controlling requirement is to ensure that the level of antihistamine remains functionally effective over 24 hours. This may require administration of the antihistamine in two or more portions, one allowing immediate release or release over an hour or so, and another one releasing at a later time, for example 12 hours later, or about 8 to 16 hours later, to sustain activity; or the antihistamine may be in a sustained release form where it is gradually released over a period so that its activity remains at a therapeutic level.

In an AM formulation, when a sedative antihistamine is used in the formulation, the non-sedating antihistamine's release will typically begin almost immediately, or within about an hour or two hours of administration. The non-sedating antihistamine will then exert an effective level of antihistamine response for a duration which preferably extends until the effects of the sedative antihistamine begin to be felt, which as noted will typically be in the range of about 12 to 18 hours. The release rates and antihistamine effective doses of the sedating and non-sedating antihistamine will be adjusted to maintain an effective but not excessive level of antihistamine activity during the initial period in which only the non-sedating antihistamine is present; during an overlap period, if required by kinetics and particularly half-lives of histamines; and optionally at a low level during the administration of the sedating histamine, to provide at least some level of antihistamine effects at all times.

The "negative" effect of sedation is used to the advantage of the patient in administration right before sleep, which allows the patient to have a good night sleep, while at the same time maintaining control of the histamine-associated allergic symptoms. Since most patients will want to sleep at night, the composition where the sedating antihistamine or other sedating drug is immediately released is referred to as the P.M. Medication, and the composition where the sedating antihistamine or other sedating drug is released beginning at least several hours after administration is referred to as the A.M. Medication.

Additional Active Ingredients

In any of the above compositions, the non-antihistamine sedative drug is optionally is a hypnotic, an anxiolytic, and a sedative. Many examples of drugs of these classes are known in the art. Other drugs, analogous to the sedative antihistamines, have sedative effects that are considered secondary to their primary, intended use; such sedative drugs may be of use as sedatives in the composition if their primary effect is compatible with the alleviation of histamine-mediated symptoms.

In any of the above compositions, additional drugs may be included that enhance the treatment or alleviation of histamine-mediated symptoms, provided that such drugs are compatible with the temporally-distinguished sedation control features. One example of such a drug type is a leukotriene receptor antagonist.

Supplementary agents can also be included in the formulation. These may be selected from one or more of analgesics, antitussive agents, expectorants, anti-inflammatory agents, anti-pyretic agents, and decongestants. These agents allow us to control symptoms that are common among patients who suffer from allergic rhinitis, common cold, flu, and various other allergic or rhinitis-stimulating reactions.

Examples of the antitussives that may be employed include caramiphen (edisylate), dextromethorphan (Hbr), codeine (phosphate, sulfate), fominoben, hydromorphone, chlophedianol, carbetapentane, and noscapine.

Examples of expectorants that may be employed include terpin hydrate, guaifenesin (glycerol guaiacolate), bromohexene, potassium guaicolsulfonate, potassium iodide, potassium citrate, ammonium chloride, N-acetyl-cysteine, and ambroxol.

Examples of analgesics and anti-inflammatory agents include acetylsalicylic acid, choline salicylate, magnesium salicylate, diflunisal, acetaminophen, meclofenamate, mefenamic acid, etodolac, diclofenac potassium, ibuprofen, fenoprofen, ketoprofen, naproxen, naproxen sodium, piroxicam, benoxaprofen, flubiprofen, fenbufen, indoprofen, pirprofen, oxaprozin, carpsofen, suprofen, alminoprofen, and tiaprofen.

Controlled Release Formulations

It is preferred that one or both of the sedating compound (preferably a sedating antihistamine) and the non-sedating antihistamine be encapsulated in or coated with a polymeric material which will delay release or cause release to be sustained over a period in excess of about one hour.

In a preferred embodiment of the once-a-day delivery of the P.M. Medication, the sedating drug is released beginning substantially immediately upon ingestion and has a sedating effect of about 2 or about 4 hours, optionally a duration of about 6 to 8 hrs, optionally up to about 12 hours, thereby controlling rhinitis and other allergic symptoms and at the same time inducing drowsiness and sleep in patients so that they can enjoy a good night sleep. Upon a patient's awakening in the morning, or earlier if the sedating antihistamine release ceases earlier, then the release of non-sedating antihistamines begins. The antihistamine effect is still provided but there is no interference with normal function. If the non-sedating antihistamine does not persist for 24 hours, whether immediately or after several days of buildup, then the sedating drug is preferably at least partially a sedating antihistamine, in order to maintain the suppression of allergic rhinitis and/or other symptoms of histamine release while sleeping. Alternatively, the non-sedating antihistamine is supplied in controlled release form, or partially in delayed release form, so that its activity is sustained through at least the waking period and optionally on a 24 hour basis.

These agents may be in immediate release form or preferably are in sustained release form. The sustained release is achieved by standard methods for formulating the particular agent into a sustained release form, allowing maintenance of desired effective levels of the agent over a selected time period. Numerous methods of achieving sustained release and controlled release are known in the art, and any of them are potentially suitable for use as described herein. Methods for providing sustained release (prolonged release) and controlled release, or release beginning at a delayed time after administration, include selection of tableting compounds, especially when coupled with control of pressures in tableting; incorporation of disintegrants into tablets; enclosing tablets in rate-controlling coatings, or coatings having a known life in the gastrointestinal system, especially coatings that pass intact through the stomach and dissolve in the intestine ("enteric coatings"); mixtures of drugs with slowly absorbed materials, such as fats; and combinations of these methods, or with other currently-known techniques.

Additional methods to formulate modified release drug compositions include complexing a drug with an ion-exchange resin in the form of small particles, typically less than 150 microns. The drug is selected based on the inclusion in the molecule of a group, such as an amino group, which will readily bind to a complexing agent such as an ion-exchange resin. Thus, any drug that bears an acidic or a basic functional group, for example, an amino group, a quaternary aliphatic or aromatic cationic group, and/or an anionic or acid group, including a carboxylic acid, phosphoric acid, phenol, sulfuric acid or sulfonic acid group, is suitable for use with an ion exchange resin. Suitable resins include, but are not limited to, Amberlite IRP-69 (Rohm and Hass) and other Amberlite ion-exchange resins, Dowex ion exchange resins, Indion 224, Indion 244, and Indion 254 (Ion Exchange (India) Ltd.), and other pharmaceutically-approved ion-exchange resins. The drug-containing complexed resin particles can be further coated by methods known in the art to provide immediate release particles, enteric coated particles, extended release particles or enteric coated, extended release particles. Additionally these particles can be formulated into tablets, capsules, solutions or suspensions, allowing other opportunities to affect the timing and rate of release of the complexed drug from the resin.

Likewise, hydrophobic drugs can be absorbed into a porous hydrophobic microparticulate material to retard their release in the body or to make it more gradual; and such microparticulates may likewise be coated, incorporated in tablets, etc.

In any formulation, the active drugs may be present as salts, labile esters, complexes, metabolites, enantiomers or stereoisomers, and other forms that are either active or activatable in vivo.

A dosage form for these uses may contain materials prepared in several ways to achieve the desired release profile. One method includes a component for delayed onset release, whether sustained or rapid, in a first physical form, preferably a form coated with a first release control material and optionally further coated with additional release-controlling layers. The physical form may, for example, be a tablet, or a spherule or other small particle, or may be a microcapsule formed by any of a variety of methods. The delayed onset component is then mixed with or coated with material for prompt release to form a dosage form. The final form itself may be coated, tableted, or encapsulated as required.

In many cases, the formation of an appropriate dosage form can be simple. For example, a "PM" (bedtime) dosage form containing a long-acting non-sedating antihistamine, such as loratidine, and a sedating histamine can be prepared by mixing small spherules of the loratidine with the sedating antihistamine, and forming a tablet. Separate coatings for the two ingredients may be provided to prevent interaction between them until administration. More preferably, to properly spread out the dosage of the combined antihistamines, the non-sedating antihistamine, or a portion thereof, can be coated with a release-delaying coating, and then the dosage form can be formed.

While solid dosage forms are convenient, the formulation can be a liquid containing both a sedating compound and a non-sedating antihistamine. In one embodiment for bedtime administration, the sedating compound can be in solution and the non-sedating antihistamine can be encapsulated or absorbed or otherwise present in a form that delays its release for an initial period of time upon administration. The delayed release form of the non-sedating antihistamine may be present as a suspension, or as an emulsion, or less preferably as larger particles that require shaking for resuspension. In another embodiment, for a PM administration, both a short-acting sedative compound and a long-acting non-sedating antihistamine can be in solution, if they are stable in solution. Alternatively, one or both of the sedating compound and the non-sedating antihistamine can be encapsulated, for example to provide stability and/or taste-masking, and may release in different manners, for example with one component having an enteric coating, or both having enteric coatings of different durabilities.

Both sustained release and delayed release are often accomplished by coating and/or compressing the drug together with sustained release and/or delayed release polymers. The delayed release or sustained-release control polymers may be any of those known in the art. Extensive lists of such excipients are found in handbooks and the like, from which appropriate polymers may be selected. The polymers listed below, without limitation or exclusion of other polymers known in the formulation art, are potentially useful as described herein.

Many polymers are known for use in controlled release, including extended release and delayed release formulations. One preferred group of polymers comprises cellulose derivatives, including cellulose in microcrystalline or powdered form, and celluloses reacted with substituents to form ethers, such as ethylcellulose, methylcellulose and other alkylcelluloses; and with substituents to form hydroxyethers, such as hydroxyethyl cellulose or hydroxypropyl cellulose; and to form esters with acids (often from anydrides) such as cellulose acetate, cellulose succinate, and cellulose phthalate; and with other reagents to form charged groups such as carboxymethylcellulose (CMC; carmelose) and its crosslinked form "crosscarmelose". Combinations of substituents are often found, including without limitation forms such as, among others, hydroxypropyl methyl cellullose (HPMC or hypromellose), HPMC acetate, HPMC succinate, HPMC phthalate, cellulose acetate trimellitate, and cellulose acetate phthalate.

A second preferred group includes polymers, copolymers, and crosslinked polymers based on acrylic groups (also known as "carboxy vinyl" groups and other older names). Preferred acrylic monomers are acrylic acid and methacrylic acid (collectively, "(meth)acrylic acids") and their esters and amides. The esters may include lower alkyl esters such as methyl and ethyl, and hydroxy esters such as hydroxyethyl and hydroxypropyl (meth)acrylates. The various monomers may be combined to produce mixed polymers, and may be crosslinked if desired by any of several di-acrylate compounds. Acrylates are typically available under various proprietary trade names, such as "Eudragit" (a polymethacrylate) and "Carbopol" (a partially crosslinked polyacrylate, also known as a carbomer.)

A third preferred group comprises natural gums and resins, which may be gelling or nongelling. The gums include alginates, carrageenans, agars, pectins, glucomannans (guar, locust bean or carob, etc.), galactomannans (e.g. konjac), and various bacterial products including xanthan and schleroglucan. Gums include gum arabic and gum traganth. Resins include shellac. Other natural products include waxes, fats, proteins (including zein and laminins), chitin, chitosan, and non-cellulosic polymeric glucoses such as starch, amylose and glycogen. Many of the gums may be found in semisynthetic form, for example propylene glycol alginate and carboxymethyl starch. In general, all of the substituents available for the celluloses are available, sometimes as commercial products, for the other natural polymers, especially the polysaccharides.

Other polymers include polyvinyl alcohol, polyvinylacetate, polyvinylpyrrolidone (povidone) and its crosslinked form crospovidone, copoly(ethylene vinylacetate (EVAC), maleic anhydride-co-alkylene copolymers ("Gantrez", e.g.), and other polymers and copolymers made from unsaturated subunits. Also included in some formulations are polyalkylene oxides, including polyethylene glycols (PEG), poloxamers, meroxapols, and other polymeric oxiranes.

The rate of delayed release of the non-sedating antihistamine in the P.M. Medication and in the delayed release of the sedating antihistamine in the A.M. Medication is controlled by at least one delayed release control polymer. A variety of such polymers are known. A preferred group comprises ethyl cellulose, cellulose acetate, cellulose acetate phthalate, hydroxypropyl methylcellulose phthalate, polyvinyl acetate phthalate, polymers and copolymers of acrylic acid, methacrylic acid, and their methyl, ethyl, hydroxyethyl and hydroxypropyl esters, hydroxyethyl methylcellulose acetate (and/or succinate), shellac, cellulose acetate trimellitate, vinyl acetate, azo polymers, pectin, chitosan, amylose, guar gum, and zein or combinations thereof. Other potentially useful polymers are listed above, or are accessible in handbooks and other sources used by formulators.

EXAMPLES

Example 1

Formulation of Sedating/Nonsedating Antihistamine for Evening Administration

Sedative antihistamine: Dexbrompheniramine
Non-sedative antihistamine: Loratadine (A) Preparation of Loratadine Tablets (Core): Each Dosage Form Contains the Following Ingredients:

| Ingredients | %/Dosage Unit (Range) | mg/Dosage Unit (A Typical Formulation) |
| --- | --- | --- |
| Loratadine | 3-5 | 7 |
| Lactose | 45-65 | 92 |
| Starch 1500 | 8-18 | 22 |
| Microcrystalline cellulose | 15-25 | 35 |
| Magnesium Stearate | 3-1 | 0.8 |
| Total | | 156.8 mg |

1. Prepare a granulation including loratadine, lactose, starch 1500 and microcrystalline cellulose.
2. Lubricate the granulation with magnesium stearate.
3. Compress the granulation into tablets about 156.8 mg weight using a suitable tablet compression machine and tooling.

(B) Enteric Coating of Loratadine Tablets (Core):

| Ingredients | %/Dosage Unit (Range) | mg/Dosage Unit (A Typical Formulation) |
| --- | --- | --- |
| Loratadine Tablets | 85-95 | 156.8 |
| Eudragit S (Rohm America) | 3-10 | 10 |
| Triethyl citrate | 1-4 | 5 |
| Glycerol monostearate | | 0.3 |
| Ammonia (from 1N Solution) | | 1.7 |
| Purified water | qs | (To be evaporated) |
| Total | | 173.8 mg |

1. Prepare an enteric coating solution including Eudragit S, triethyl citrate, glycerol monostearate and ammonia solution in purified water.
2. Coat loratadine tablets (from step (A)) with the enteric coating solution using a conventional coating pan or a fluidized-bed coating apparatus until a desired amount of coating is applied.

(C) Coating of Loratadine Enteric Coated Tablets with a Film Coat Containing Dexbrompheniramine Maleate:

| Ingredients | %/Dosage Unit (Range) | mg/Dosage Unit (A Typical Formulation) |
|---|---|---|
| Loraradine enteric coated tablets | 88-98 | 173.8 |
| Dexbrompheniramine maleate | 1-3 | 3 |
| Maleic Acid | 1-4 | 2 |
| Opadry (Film coat material from Colorcon) | 2-6 | 6 |
| Purified water | qs | (To be evaporated) |
| Total | | 184.8 mg |

Formulation:
1. Dissolve dexbrompheniramine maleate and maleic acid in purified water and disperse Opadry in the solution.
2. Coat loratadine enteric coated tablets from (B) with coating solution containing dexbrompheniramine maleate using a conventional coating pan or a fluid bed coating equipment until a desired amount of dexbrompheniramine maleate is applied.

Each finished tablet contains:
(1) 3 mg dexbrompheniramine maleate in the outer coating for immediate release.
(2) 7 mg loratadine which is enteric coated for a delayed release 4-8 hours after administration.

The film coat may be replaced with a sugar coat or compression coat which contains 3 mg dexbrompheniramine maleate.

Example 2

Formulation of Non-Sedating/Sedating Antihistamine for Morning Administration

Sedative antihistamine: diphenhydramine hydrochloride
Non-sedative antihistamine: fexofenadine hydrochloride (A) Preparation of Diphenhydramine Hydrochloride Beads: Each Dosage Form Contains the Following Ingredients:

| Ingredients | %/Dosage Unit (Range) | mg/Dosage Unit (A Typical Formulation) |
|---|---|---|
| Diphenhydramine hydrochloride | 40-70 | 50 |
| Microcrystalline cellulose | 30-60 | 35 |
| Methyl cellulose | 2-5 | 2.5 |
| Sodium starch glycolate | 5-3 | 1.3 |
| Purified water | qs | (To be evaporated) |
| Total | | 89 mg |

1. Blend diphenhydramine hydrochloride, microcrystalline cellulose, methyl cellulose and sodium starch glycolate to form uniform blend.
2. Add suitable amount of water slowly to the blend and mix.
3. The resulting granulate is extruded at high speed through a 1.0-2.0 mm plate and spheronized using an extruder/spheronizer. The spheres are then dried to moisture content of less than 7%.

(B) Enteric Coating of Diphenhydramine Hydrochloride Beads:

| Ingredients | %/Dosage Unit (Range | mg/Dosage Unit (A Typical Formulation) |
|---|---|---|
| Diphenhydramine hydrochloride beads | 60-90 | 89 |
| Eudragit S (Rohm America) | 5-15 | 12 |
| Triethyl citrate | 2-8 | 6 |
| Talc | 1-4 | 3 |
| Ammonia (From 1N solution) | 1-3 | 2.1 |
| Purified water | qs | (To be evaporated) |
| Total | | 112.1 mg |

1. Prepare an enteric coating solution including Eudragit S, triethyl citrate, talc and ammonia solution in purified water.
2. Coat diphenhydramine hydrochloride beads (from step (A)) with the enteric coating solution using a conventional coating pan or a fluidized-bed coating apparatus until a desired amount of coating is applied.
3. The enteric coated beads may be further coated with protective film coat or sugar coats using conventional coating procedure.

(C) Preparation of a Granulation Containing Fexofenadine Hydrochloride and Diphenhydramine Hydrochloride Enteric Coated Beads:

| Ingredients | %/Dosage Unit (Range) | mg/Dosage Unit (A Typical Formulation) |
|---|---|---|
| Fexofenadine hydrochloride | 25-50 | 90 |
| Pregelatized starch 1500 | 5-10 | 20 |
| Microcrystalline cellulose | 10-30 | 50 |
| Magnesium stearate | 2-1 | 0.8 |
| Purified water | qs | (To be evaporated) |
| Diphenhydramine hydrochloride enteric coated beads | 35-45 | 112.1 |
| Total | | 272.4 mg |

1. Blend fexofenadine hydrochloride, pregelatized starch and microcrystalline cellulose and granulate the blend with purified water. Dry the granulation and mill to desired particle size.
2. Blend fexofenadine hydrochloride granulation (step 1) with diphenhydramine hydrochloride enteric coated beads and blend with magnesium stearate.
3. Encapsulate the blend into capsules of suitable size. Each capsule contains 50 mg diphenhydramine hydrochloride as enteric coated beads and 90 mg fexofenadine hydrochloride as an immediate release granule.

Note: Amount of diluents such as microcrystalline cellulose and starch may be varied in order to fill the volume of a selected capsule size.

Each finished dosage form contains:
(3) 90 mg fexofenadine hydrochloride for immediate release; and
(4) 50 mg diphenhydramine hydrochloride which is enteric coated for a delayed release 8 to 12 hours after administration.

Example 3

Formulation of Sedating/Non-Sedating Antihistamine Plus a Decongestant for Evening Administration Sedative antihistamine: dexbrompheniramine maleate
Non-sedative antihistamine: cetirizine
Decongestant: pseudoephedrine sulfate (A) Preparation of Cetirizine Beads: Each Dosage Form Contains the Following Ingredients:

| Ingredients | %/Dosage Unit (Range) | mg/Dosage Unit (A Typical Formulation) |
|---|---|---|
| Cetirizine | 40-70 | 7 |
| Microcrystalline cellulose | 30-60 | 5 |
| Methylcellulose | 2-5 | 0.5 |
| Crosscarmellose sodium | 5-3 | 1 |
| Purified water | qs | (To be evaporated) |
| Total | | 156.8 mg |

1. Blend cetirizine, microcrystalline cellulose, methyl cellulose and crosscarmellose sodium to form uniform blend.

2. Add suitable amount of water slowly to the blend and granulate.

3. The resulting granulate is extruded at high speed through a 1.0-2.0 mm plate and spheronized using an extruder/spheronizer. The spheres are then dried to moisture content of less than 7%.

(B) Enteric Coating of Cetirizine Beads:

| Ingredients | %/Dosage Unit (Range) | mg/Dosage Unit (A Typical Formulation) |
|---|---|---|
| Cetirizine | 60-90 | 13.5 |
| Eudragit S (Rohm America) | 5-15 | 1.8 |
| Triethyl citrate | 2-8 | 0.9 |
| Talc | 1-4 | 0.5 |
| Ammonia (From 1N solution) | 1-3 | 0.3 |
| Purified water | qs | (To be evaporated) |
| Total | | 17.0 mg |

1. Prepare an enteric coating solution including Eudragit S, triethyl citrate, talc and ammonia solution in purified water.

2. Coat cetirizine beads (from step (A)) with the enteric coating solution using a conventional coating pan or a fluidized-bed coating apparatus until a desired amount of coating is applied.

3. The enteric coated beads may be further coated with a protective film coat or sugar coats using a conventional coating procedure.

(C) Preparation of a Granulation Containing Dexbrompheniramine Maleate, Pseudoephedrine Sulfate, and Cetirizine Enteric Coated Beads:

| Ingredients | %/Dosage Unit (Range) | mg/Dosage Unit (A Typical Formulation) |
|---|---|---|
| Dexbrompheniramine maleate | 5-4 | 3 |
| Pseudoephedrine sulfate | 0-20 | 30 |
| Lactose | 40-80 | 145 |
| Pregelatized starch 1500 | 5-20 | 25 |
| Microcrystalline cellulose | 10-30 | 45 |
| Magnesium stearate | 2-1 | 1.1 |
| Purified water | qs | (To be evaporated) |
| Cetirizine enteric coated beads | 5-20 | 17 |
| Total | | 266.1 mg |

1. Blend dexbrompheniramine maleate, pseudoephedrine sulfate, lactose, pregelatized starch and microcrystalline cellulose and granulate the blend with purified water. Dry the granulation and mill to desired particle size.

2. Blend dexbrompheniramine maleate granulation (step 1) with cetirizine enteric coated beads and blend with magnesium stearate.

(D) Preparation of a Granulation Containing Pseudoephedrine Sulfate:

| Ingredients | %/Dosage Unit (Range) | mg/Dosage Unit (A Typical Formulation) |
|---|---|---|
| Pseudoephedrine sulfate | 15-40 | 210 |
| Dibasic calcium phosphate dihydrate | 10-30 | 100 |
| Hydroxypropyl methylcellulose 2208 | 35-55 | 350 |
| Ethylcellulose | 10-30 | 100 |
| Methylcellulose | 3-10 | 50 |
| Silicon dioxide | 5-2 | 8 |
| Stearic Acid | 2-1 | 6 |
| Magnesium stearate | 2-1 | 4 |
| Total | | 828 mg |

1. Prepare a coating solution of methylcellulose in water.

2. Blend pseudoephedrine sulfate, dibasic calcium phosphate dihydrate, hydroxypropyl methylcellulose 2208, and ethylcellulose and mix.

3. Granulate the blend from step 2 with methylcellulose solution from step 1. Pass the granulation through a screen with a desired mesh size.

4. Dry the granulation until moisture content is less than 3.0%.

5. Mill or pass the dried granulation through a screen with a desired mesh size.

6. Blend the milled granulation with silicon dioxide, stearic acid and magnesium stearate (E) Compression of the Double-Layer Finished Product Tablets Using Granulations from Steps (C) and (D):

| Ingredients | %/Dosage Unit (Range) | mg/Dosage Unit (A Typical Formulation) |
|---|---|---|
| Granulation (C) | 15-40 | 266.1 |
| Granulation (D) | 10-30 | 828 |
| Total | | 1094.1 mg |

A tablet compression apparatus capable of compressing a multi-layer tablet is used to compress 266.1 mg of granulation (C) in one layer and 828 mg of granulation (D) in the second layer.

Each finished double-layer tablet contains the following active ingredients:

(1) The first layer contains:
 (a) 3 mg dexbrompheniramine maleate and 30 mg pseudoephedrine sulfate for immediately release.
 (b) 7 mg cetirizine which is enteric coated for delayed release 4-8 hours after administration.

(2) The second layer contains 210 mg pseudoephedrine sulfate for sustained release over 24 hours.

In order to allow an easier swallowing, the amount for one dosage unit (1094.1 mg) may be divided into two double-layer tablets each contains 547 mg (133 mg granulation C first layer and 414 mg granulation D the second layer). In this case, the patient will be instructed to take two tablets instead of one tablet per dose.

Example 4

Formulations with Encapasulated Loratidine (6-8 Hour and 1-3 Hour Release) and Immediate Release Sedating Histamine Component for PM Administration (A) Preparation of Loratadine Tablets (Core): Each Dosage Unit Contains the Following Ingredients:

| Ingredients | Quantity per batch (g) |
|---|---|
| Loratadine | 50.00 |
| Directly compressible Lactose | 200.00 |
| Pregelatinized corn Starch | 50.00 |
| Microcrystalline Cellulose | 100.00 |
| Magnesium Sterate | 4.00 |
| Colloidal Silicon Dioxide | 2.50 |
| Total | 406.50 |

1. Loratadine, Directly compressible Lactose, Microcrystalline Cellulose, and Pregelatinized Corn Starch were passed through a #30 screen and mixed for 2 minutes.

2. Instruction 1 was lubricated with Magnesium Stearate and Colloidal Silicon Dioxide, which were already passed through a #60 screen for 1 minute.

3. Granulation was compressed on a single station compression machine fitted with a 3/16 round punch set with the following tablet parameters:
 Weight: 81.3 mg
 Hardness: 7-8 kP
 Friability: <1.0%
 Disintegration Test: <5 minutes.

(B) Enteric Coating of Loratadine Tablets (6-8 hr):

| Ingredients | Quantity per batch (g) |
|---|---|
| Loratadine Tablets (Formulation A). | 50.00 |
| Placebo Tablets | 650.00 |
| Eudragit S 100 Powder | 175.00 |
| Triethyl Citrate | 122.50 |
| 1N Strong Ammonia (1.7%) | 89.07 |
| Talc USP | 17.50 |
| D&C Yellow # 10 Al. Lake | 0.06 |
| Purified Water USP | 1220.00 (to be evaporated) |

Preparation of Coating Solution:

1. Eudragit S 100 powder was dispersed in Purified Water. Mixing was continued for 10 minutes to form a homogeneous dispersion.

2. 1.7% ammonia solution was prepared from 1N Strong Ammonia solution and Purified Water.

3. Dilute ammonia (1.7%) solution was added slowly while mixing and mixing was continued for 60 minutes.

4. Triethyl Citrate was added and mixing was continued for 60 minutes. It was kept under slow mixing until next day morning.

5. Talc powder and D&C Yellow #10 Aluminium Lake were dispersed into Purified Water in a separate stainless stell container and mixed for 15 minutes. It was mixed at high speed for 10 more minutes and kept under slow mixing until next day morning.

6. Pigment suspension was added and mixed for 5 minutes.

7. The suspension was filtered through # 100 mesh screen and kept under slow constant stirring before and during coating.

Coating was performed in the Wuster column of Glatt GPCG1 fluid bed coater. The coating solution was applied with the following coating parameters until 40% coating weight gain obtained.

Coating Parameters:
 Coating Load: 700 g
 Spray Rate: 4.9-6.00 g/min
 Atomizing Air Pressure 2 Bar
 Inlet Air Temperature: 43-46° C.
 Product Temperature: 35-37° C.

A sample was collected after 30% coating weight gain. At the end of the coating and before collecting each sample, tablets were dried for 10 minutes without spray.

(C) Enteric coating of Loratadine tablets (1-3 hr):

| Ingredients | Quantity per batch (g) |
|---|---|
| Loratadine Tablets (Formulation A). | 60.00 |
| Placebo Lactose Pellets | 640.00 |
| Acryl Eze White 93018359 (ready to use enteric mixture) Contains Methacrylic Acid Coplymer Type C, USP NF (Methacrylic Acid-Ethylacrylate 1:1 copolymer) and other coating ingredients | 254.80 |

-continued

| Ingredients | Quantity per batch (g) |
|---|---|
| Simethicone Emulsion USP (Dow Corning 7-9245 (30%) | 1.27 |
| FD&C Blue # 1 Lake Concentrate | 0.26 |
| D&C Red # 33 Aluminium Lake | 0.26 |
| Purified Water USP | (To be evaporated) |
| Total | 1019.00 |

Preparation of Coating Solution:

1. Simethicone Emulsion and colors were added to Purified Water and mixed vigorously for 2 minutes.

2. Acryl-Eze® white powder was dispersed into the solution and mixed for 60 minutes to form a homogeneous dispersion.

3. The suspension was filtered through a #100 mesh screen and kept under slow constant stirring before and during coating.

Coating was performed in the Wuster column of Glatt GPCG1 fluid bed coater. Coating solution was applied with the following coating parameters until 21.90% coating weight gain obtained.

Coating Parameters:
 Coating Load: 700 g
 Spray Rate: 8-10.2 g/min
 Atomizing Air Pressure 1.2 Bar
 Inlet Air Temperature: 42-43° C.
 Product Temperature: 36-37° C.

Samples were collected after 17.3%, 20.5% and 21.9% coating weight gain. All samples were dried for 10 minutes in oven at 40° C.

(D) Preparation of Diphenhydramine Hydrochloride Granulation: Each 45.75 mg of Granulation Contains the Following Ingredients:

| Ingredients | mg/Dosage unit |
|---|---|
| Diphenhydramine Hydrochloride | 25 |
| Microcrystalline Cellulose | 20.00 |
| Magnesium Stearate | 0.75 |
| Total | 45.75 |

1. Sift Diphenhydramine Hydrochloride and Microcrystalline Cellulose through a 30 # screen and mix them for 3 minutes.

2. Lubricate the instruction 1 granulation with Magnesium Stearate, previously passed through a #60 screen, for 1 minute.

(E) Preparation of Capsules with Sedating and Non-Sedating Portions:

Diphenhydramine Hydrochloride immediate release granulation (sedating), equivalent to 25 mg of Diphenhydramine Hydrochloride Formulation D, and Loratadine delayed release coated tablets (non-sedating) equivalent to Loratadine 10 mg Formulation B with 30% weight gain, were filled into each capsule.

(F) Preparation of Capsules with Sedating and Non-Sedating Portions:

Diphenhydramine Hydrochloride immediate release granulation (sedating), equivalent to 25 mg of Diphenhydramine Hydrochloride Formulation D, and Loratadine delayed release coated tablets (non-sedating) equivalent to Loratadine 10 mg Formulation C with 20.5% weight gain, were filled into each capsule.

Capsules of Formulation E and Formulation F were subjected to dissolution with the following parameters:
 (a) Media: 0.1N HCL, pH 6.8 Phosphate buffer, pH 7.0 Phosphate buffer and pH 7.5 Phosphate buffer.
 (b) Volume: 900 ml
 (c) Time points: 0-2 hours in 0.1N HCL, 2-4 hours in pH 6.8 Phosphate buffer, 4-6 hours in pH 7.0 Phosphate buffer and 6-10 hours in pH 7.5 Phosphate buffer.
 (d) Apparatus: 2 (Paddle)
 (e) Speed: 50 rpm The following release profiles were obtained for Formulation E and Formulation F capsules:

| | Formulation E % released | | Formulation F % released | |
|---|---|---|---|---|
| Time (hours) | Diphenhydramine Hydrochloride | Loratadine | Diphenhydramine Hydrochloride | Loratadine |
| 1 | 100 | 0 | 100 | 0 |
| 2 | 99 | 0 | 99 | 0 |
| 3 | 0 | 0 | 0 | 100 |
| 4 | 0 | 0 | 0 | 98 |
| 5 | 0 | 0 | 0 | 100 |
| 6 | 0 | 0 | — | — |
| 6.5 | 0 | 66 | — | — |
| 7.0 | 0 | 90 | — | — |
| 8 | 0 | 98 | — | — |
| 9 | 0 | 99 | — | — |
| 10 | 0 | 100 | — | — |

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A biphasic antihistamine composition in daily oral uni-dosage or divided dosage form which comprises:
 (a) a therapeutically effective amount of a sedating antihistamine to inhibit histamine release for a duration of about 4 to 12 hours, and
 (b) a therapeutically effective amount of non-sedating antihistamine to inhibit histamine release for a duration of 10 to 20 hours, with a delayed release 1 to 10 hours after ingestion, wherein the delayed release portion is achieved by coating a core, granulations, or microcapsules with at least one delayed release polymer.

2. The antihistamine composition of claim 1, wherein the non-sedating antihistamine is released two to six hours after administration.

3. The antihistamine composition defined in claim 1 wherein the sedating antihistamine is selected from the group consisting of brompheniramine, chiorpheniramine, debrompheniramine, dexchlorpheniramine, carbinoxamine, clemastine, diphenhydramine, pyrilamine, tripelennamine, tripolidine, methdilazine, bromodiphenhydramine, promethazine, azatadine, cyproheptadine, diphenylpyraline, doxylamine, trimeprazine, phenindamine, ketotifen, hydroxyzine, tazifylline, temelastine, meclizine, acrivastine, setastine, oxatomide, mequitazine, levocabastine, lodoxamide, AHR 11325, phenindamine, azelastine, and ebastine, or a pharmaceutically acceptable salt thereof.

4. The antihistamine composition defined in claim 1 wherein the non-sedating antihistamine is selected from the group consisting of fexofenadine, loratadine, descarboethoxy loratadine, astemizole, norastemizole, desmethylastemizole, cetirizine, acrivastine, and temelastine, or a pharmaceutically acceptable salt thereof.

5. The antihistamine composition defined in claim 1 wherein the sedating antihistamine has a duration of activity of about 6 to 10 hours.

6. The antihistamine composition defined in claim 1 wherein the non-sedating antihistamine has a duration of activity of about 12 to 18 hours.

7. The antihistamine composition defined in claim 1 wherein the sedating antihistamine is releasable immediately or up to 1 hour following administration.

8. The antihistamine composition defined in claim 1 which further comprises a therapeutically effective amount of at least one agent selected from the group consisting of an analgesic agent, an antitussive agent, an expectorant, an anti-inflammatory agent, an anti-pyretic agent and a decongestant.

9. The antihistamine composition defined in claim 1 wherein the at least one delayed release polymer is selected from the group consisting of ethyl cellulose, cellulose acetate, cellulose acetate phthalate, hydroxypropyl methylcellulose phthalate, polyvinyl acetate phthalate, acrylic acid polymers and copolymers, polymers or copolymers of methacrylic acid, methyl acrylate, ethyl acrylate, methyl methacrylate, ethyl methacrylate, hydroxypropyl methylcellulose acetate succinate, shellac, cellulose acetate trimellitate, vinyl acetate, azo polymers, pectin, chitosan, amylose, guar gum, and zein or combination thereof.

10. The antihistamine composition defined in claim 8 wherein the analgesic agent, antitussive agent, expectorant, anti-inflammatory agent or decongestant is in a sustained release form.

11. The antihistamine composition defined in claim 10 wherein the sustained release effect is achieved by formulating the analgesic agent, antitussive agent, expectorant, anti-inflammatory agent or decongestant with a sustained-release control polymer selected from the group consisting of methyl cellulose, ethyl cellulose, wax, gums, cellulose acetate, cellulose acetate phthalate, hydroxypropylmethylcellulose succinate, polyvinyl acetate phthalate, acrylic acid polymers and copolymers, polymers or copolymers of methacrylic acid, methyl acrylate, ethyl acrylate, methyl methacrylate, ethyl methacrylate, hydroxypropyl methylcellulose acetate succinate, shellac, cellulose acetate trimellitate, vinyl acetate and combination thereof.

12. A method of inhibiting the release of histamine in a patient which comprises the step of administering to the patient, a therapeutically effective amount of the antihistamine composition defined in claim 1.

13. The method of inhibiting the release of histamine defined in claim 12 wherein the antihistamine composition is administered during the evening or night and the sedating antihistamine is immediately released.

14. The method of inhibiting the release of histamine defined in claim 12 wherein the antihistamine composition is administered during the evening or night and the non-sedating antihistamine is released the next day, 6 to 10 hours following administration.

15. The method of inhibiting the release of histamine defined in claim 12 wherein the patient suffers from allergic reaction, allergic rhinitis, cold or flu.

\* \* \* \* \*

UNITED STATES PATENT AND TRADEMARK OFFICE
CERTIFICATE OF CORRECTION

| | | |
|---|---|---|
| PATENT NO. | : 7,585,520 B2 | Page 1 of 1 |
| APPLICATION NO. | : 10/943311 | |
| DATED | : September 8, 2009 | |
| INVENTOR(S) | : Mark Hirsh et al. | |

It is certified that error appears in the above-identified patent and that said Letters Patent is hereby corrected as shown below:

On the title page, Item (*) Notice should read:

Subject to any disclaimer, the term of this patent is extended or adjusted under 35 U.S.C. 154(b) by 1139.

Claim 3, column 19, line 3, replace "chiorpheniramine" with --chlorpheniramine--.

Signed and Sealed this

Seventeenth Day of August, 2010

David J. Kappos
*Director of the United States Patent and Trademark Office*

UNITED STATES PATENT AND TRADEMARK OFFICE
CERTIFICATE OF CORRECTION

PATENT NO. : 7,585,520 B2 Page 1 of 1
APPLICATION NO. : 10/943311
DATED : September 8, 2009
INVENTOR(S) : Hirsh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1139 days.

Signed and Sealed this

Fourteenth Day of September, 2010

David J. Kappos
*Director of the United States Patent and Trademark Office*